US008586074B2

(12) United States Patent
Mamidwar et al.

(10) Patent No.: US 8,586,074 B2
(45) Date of Patent: Nov. 19, 2013

(54) CALCIUM SULFATE COMPOSITE PARTICLES INCLUDING AGGREGATED CALCIUM SULFATE NANOPARTICLES AND METHOD OF USE FOR BONE AUGMENTATION

(75) Inventors: Sachin Mamidwar, Jersey City, NJ (US); Harold Alexander, Short Hills, NJ (US); John L. Ricci, Middletown, NJ (US)

(73) Assignee: Orthogen, LLC, Springfield, NJ (US)

( * ) Notice: Subject to any disclaimer, the term of this patent is extended or adjusted under 35 U.S.C. 154(b) by 0 days.

(21) Appl. No.: 13/366,517

(22) Filed: Feb. 6, 2012

(65) Prior Publication Data

US 2012/0203356 A1    Aug. 9, 2012

Related U.S. Application Data

(60) Provisional application No. 61/440,554, filed on Feb. 8, 2011.

(51) Int. Cl.
*A61F 2/02* (2006.01)
(52) U.S. Cl.
USPC .......................................................... 424/426

(58) Field of Classification Search
None
See application file for complete search history.

(56) References Cited

U.S. PATENT DOCUMENTS 6,030,636 A * 2/2000 Randolph et al. ............. 424/426
7,767,226 B2 * 8/2010 Park et al. ..................... 424/464

* cited by examiner

*Primary Examiner* — Carlos Azpuru
(74) *Attorney, Agent, or Firm* — CUSPA Technology Law Associates; Yi Li (57) ABSTRACT

Calcium sulfate composite particles for bone augmentation are disclosed. The composite particles are composed of aggregated calcium sulfate nanoparticles of a diameter from about 50 to about 800 nm, which include a mixture of calcium sulfate dihydrate and calcium sulfate hemihydrate. The composite particles have a diameter from about 200 to about 1,200 µm, and a mean half-life no less than 18 days. Further disclosed is a bone grafting material for bone augmentation. The bone grafting material includes a mixture of the calcium sulfate composite particles and a second type of calcium sulfate particles having a particle diameter from about 2 to about 60 µm, at a ratio from 1:1 to 4:1. The method of using the composite particles and the bone grafting material for bone augmentation is also disclosed.

16 Claims, 7 Drawing Sheets

CALCIUM SULFATE COMPOSITE PARTICLES INCLUDING AGGREGATED CALCIUM SULFATE NANOPARTICLES AND METHOD OF USE FOR BONE AUGMENTATION

CROSS REFERENCE TO RELATED APPLICATION

This application claims the benefit under 35 USC 119 (e) of the provisional patent application Ser. No. 61/440,554, filed Feb. 8, 2011, which is hereby incorporated by reference in its entirety.

FIELD OF THE INVENTION

The present invention relates to calcium sulfate material for bone augmentation, more specifically, relates to calcium sulfate composite particles comprising aggregated calcium sulfate nanoparticles and method of use.

BACKGROUND OF THE INVENTION

Repairing bone defects and augmentation of existing bone often require the use of bio-resorbable materials, which may include autogenous bone graft, allogeneic bone graft, or alloplastic materials. Synthetic bone graft materials are alternatives to autogenous and allogenic bone, and these include calcium phosphates, calcium sulfate, hydroxyapatite, resorbable polymers, bioglass, and various combinations of bone derivatives. Calcium sulfate has been used for many years in dentistry and medicine. In its hemihydrate form, calcium sulfate has been used as a bone graft material and is known as a biocompatible, completely biogradable, and safe material. It has further been demonstrated in animal and clinical studies to have osteoconductive stimulation property that can be used for bone augmentation and improving the repair of bone defects.

Previous research of the present inventors has shown that calcium sulfate causes precipitation of calcium phosphate deposits as it dissolves at the surgical site. These precipitates stimulate and direct the formation of new bone. Moreover, to achieve optimal result, it is desirable that calcium sulfate, calcium phosphate, or any other bone repair materials stay at the surgical site for a considerable period of time, in order to inhibit soft tissue filling of the defect and to effectively stimulate bone growth.

However, when conventional calcium sulfate is used as a cement to fill a bone void, fracture, or other defects in human bone, this material dissolves at a rapid rate, with a complete dissolution in about four weeks, and cannot be retained at the site for longer periods. As such, the principal concern and deficiency with the conventional calcium sulfate are that calcium sulfate dissolves too rapidly at a recipient site, this outpaces the formation of new bone in human patients. Therefore, a need arises for improved calcium sulfate material which degrades at the recipient site in a rate desirably matching the rate of bone growth.

Recently, Ricci et al (U.S. Pat. No. 6,770,695 B2) disclose polymer containing calcium sulfate particles that comprise resorbable polymers mixed with or coated on calcium sulfate. The resorbable polymers slow down dissolution of the particles in the recipient site and improve the effect of the grafting material in bone augmentation and repairing. However, polymers are more expensive, which increases the cost of the implant material. Moreover, polymers, such as commonly used polylactic acid and polyaspirin, could have negative effect on bone formation. Polylactic acid releases acidic degradation products which could potentially lead to bone resorption rather than bone formation, especially when used in high quantities. Polyaspirin releases salicylic acid as a result of its degradation, which may also potentially lead to bone resorption when used in high quantities.

On the other hand, Park et al (U.S. Pat. No. 7,767,226) recently disclose hemihydrate calcium sulfate nanoparticles and method of use in facilitating bone repair. Park et al disclose various known methods for producing calcium sulfate nanoparticles. More specifically, microemulsion technique for making calcium sulfate dihydrate nanoparticles has been described by Rees, et al. (Langmuir 15 (1999) 1993-2002). Another method is cryo-vacuum technique described Salvadori, et al. (Journal of Colloid and Interface Science, 2005, 1-4). This technique involves quick freezing a solution of conventional calcium sulfate and dehydrating the frozen ice of the solution of calcium sulfate under vacuum (lyophilization). Moreover, in order to form hemihydrate nanoparticles, the freeze-dried crystals can be heated and dried in an oven to obtain β-form calcium sulfate hemihydrate nanoparticles. α-form calcium sulfate hemihydrate nanoparticles can be obtained by autoclaving the calcium sulfate dihydrate nanoparticles.

Park et al further disclose compositions comprising hemihydrate calcium sulfate nanoparticles and a growth factor, such as PDGF, IGF-I, TGF-β and others. As demonstrated by the release of PDGF, Park et al disclose that calcium sulfate nanoparticles degrade faster than conventional calcium sulfate. This is thought to be beneficial for rapid release of the growth factor. However, as discussed above, faster dissolution of calcium sulfate nanoparticles is undesirable, because it outpaces the formation of new bone.

Therefore, there is a need for improved calcium sulfate particles and bone grafting materials for repairing bone defects and augmentation of existing bone.

SUMMARY OF THE INVENTION

In one embodiment, the present invention is directed to calcium sulfate composite particles for bone augmentation and repair. The calcium sulfate composite particles comprise aggregated calcium sulfate nanoparticles of a diameter from about 50 to about 800 nanometers, the calcium sulfate nanoparticles comprising a mixture of calcium sulfate dihydrate and calcium sulfate hemihydrate; the composite particles having a diameter from about 200 to about 1,200 micrometers, and having a mean half-life no less than 18 days.

In a further embodiment, the present invention is directed to a bone grafting material for bone augmentation and repair. The bone grafting material comprises calcium sulfate composite particles of the present invention and a second type of calcium sulfate particles having a particle diameter from about 2 to about 60 µm, wherein a ratio of the calcium sulfate composite particles to the second type of calcium sulfate particles in the bone grafting material is from 1:1 to 4:1. The second type of calcium sulfate particles can be calcium sulfate hemihydrate, calcium sulfate dihydrate, or mixture thereof.

In another embodiment, the present invention is directed to a method of bone augmentation. The method comprises mixing a bone grafting material with a setting agent to form a composition, the bone grafting material comprising the calcium sulfate composite particles of the present invention; and applying the composition to a recipient site; wherein the calcium sulfate composite particles degrade substantially linearly at a rate determined by the mean half-life, and affect a prolonged stimulation to bone growth in the recipient site.

In a further embodiment, the bone grafting material further comprises a second type of calcium sulfate particles having a particle diameter from about 2 to about 60 μm, wherein a ratio of the calcium sulfate composite particles to the second type of calcium sulfate particles in the bone grafting material is from 1:1 to 4:1; and wherein the formed composition comprises the calcium sulfate composite particles dispersed in a matrix formed by the second type of calcium sulfate particles.

The composite particles, bone grafting material, or the formed composition of the present invention may further comprise one or more growth factors for stimulating bone growth, or may further comprise one or more antibiotics for treating infection and bone defects at the same time.

The advantages of the present invention will become apparent from the following description taken in conjunction with the accompanying drawings showing exemplary embodiments of the invention.

BRIEF DESCRIPTION OF DRAWINGS

It is noted that in the drawings like numerals refer to like components.

DETAILED DESCRIPTION OF THE INVENTION

In one embodiment, the present invention provides novel calcium sulfate composite particles for bone augmentation. The calcium sulfate composite particles comprise aggregated calcium sulfate nanoparticles having a diameter from about 50 to about 800 nanometers (nm), inclusive of the recited upper and lower diameter size limits. The calcium sulfate composite particles have a diameter from about 200 to about 1,200 micrometers (μm), preferably from about 400 to about 1,000 μm. The calcium sulfate nanoparticles comprise a mixture of calcium sulfate dihydrate and calcium sulfate hemihydrate, and are crystalline in nature.

The term "calcium sulfate composite particles" used herein refers to larger particles comprising therein aggregated calcium sulfate nanoparticles having a diameter in the nanometer range defined above, wherein the nanoparticles are a mixture of calcium sulfate dihydrate and calcium sulfate hemihydrate. The calcium sulfate composite particles are substantially free of organic solvent and synthetic polymers.

In one exemplary embodiment, the calcium sulfate composite particles are produced by a concurrent aqueous surface spray wetting and rotational mixing process. More specifically, conventional calcium sulfate hemihydrate particles are used as the starting material. Conventional calcium sulfate hemihydrate particles ($CaSO_4 \cdot 1/2H_2O$) are commercially available. Preferably, medical grade calcium sulfate hemihydrate is used as the starting material for producing the composite particles of the present invention. Commercially available medical grade calcium sulfate hemihydrate particles may have a broad size range depending on the manufacturing process, and the particle diameters can be from 2 to 60 μm. Water, and preferably deionized water, is used in the process. Other suitable aqueous media, such as alkaline metal salt solution, for example saline, may also be used.

In one embodiment, a rotational drum mixer equipped with a sprayer therein is used for producing the composite particles. Medical grade conventional calcium sulfate hemihydrate particles in the form of fine powder is loaded in the drum mixer. Water is sprayed on to the calcium sulfate hemihydrate particles, while the particles are rotationally mixed by the drum mixer for a period of time. At the same time, the drum mixer is heated to an elevated temperature from about 30° C. to about 70° C. during the spray. The water is adjusted to a form of mist, sufficient to wet the exterior surface of calcium sulfate hemihydrate particles, for example, at approximately 20 to 50 grams per minute. The spraying may be continuous, or segmented, for approximately 20 to 60 minutes. During the spraying, the drum mixer may typically rotate at a speed between 300 and 600 RPM. The drum speed may be constant or vary. The formed larger particles are then air dried in the drum mixer at the elevated temperature described above for a period of time sufficient to remove free water. During the drying process the mixer speed may reduce down from the speed during spraying, for example down to half. The drying process is complete when the exhaust air temperature starts rising. This results in a dry powder of the composite particles.

During the above production process several changes occur. Chemically, conversion of the wetted particles from the original calcium sulfate hemihydrate to calcium sulfate dihydrate ($CaSO_4 \cdot 2H_2O$) occurs according to the following equation:

$$CaSO_4 \cdot 1/2H_2O + 1\tfrac{1}{2}H_2O = CaSO_4 \cdot 2H_2O$$

Concurrent with the chemical conversion, structurally the original micrometer size particles break down and transform to crystalline particles having a size in the nanometer range. Meanwhile, under the surface wetting and rotational mixing condition, these nanoparticles aggregate and form larger composite particles having a diameter in a range from about 200 to about 1,200 μm. Consequently, it has been found that the formed larger particles are not simple aggregations of the original calcium sulfate hemihydrate particles, rather they are composite particles comprising aggregated crystalline nanoparticles that include a mixture of both calcium sulfate dihydrate and calcium sulfate hemihydrate.

Figure 1:
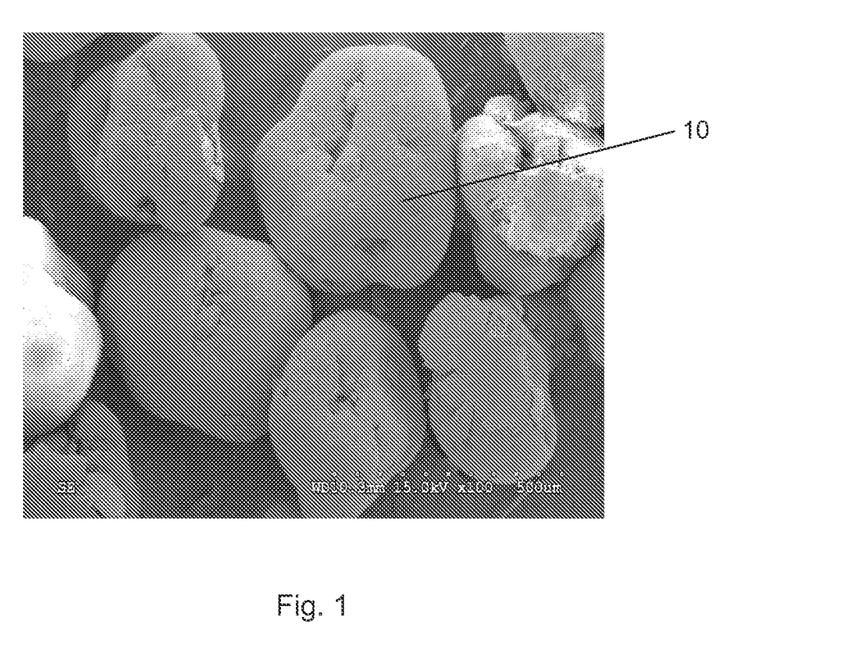
FIG. 1 is a SEM image of the calcium sulfate composite particles of the present invention at 100× magnification.
Figure 2:
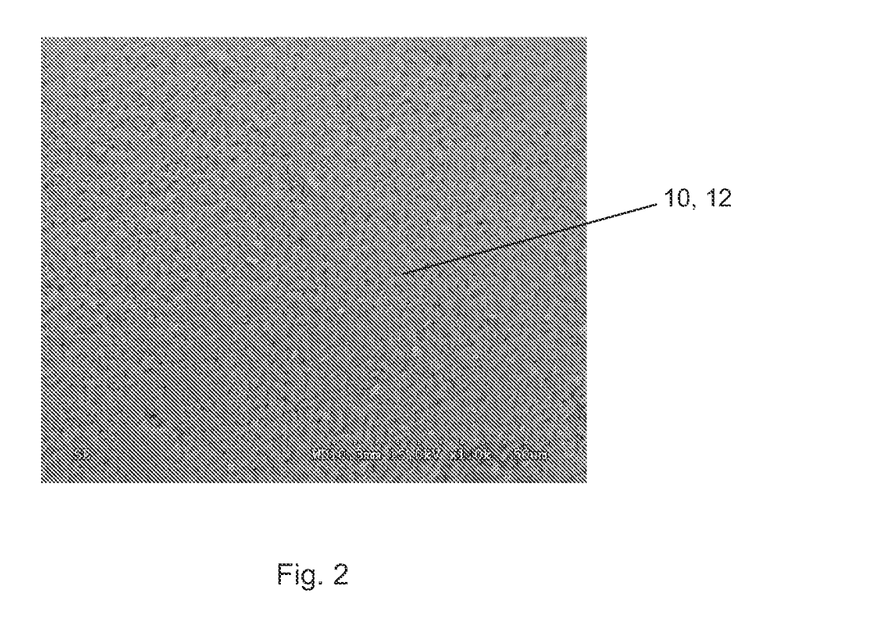
FIG. 2 is a SEM image of the surface of a calcium sulfate composite particle at 1000× magnification.
Figure 3:
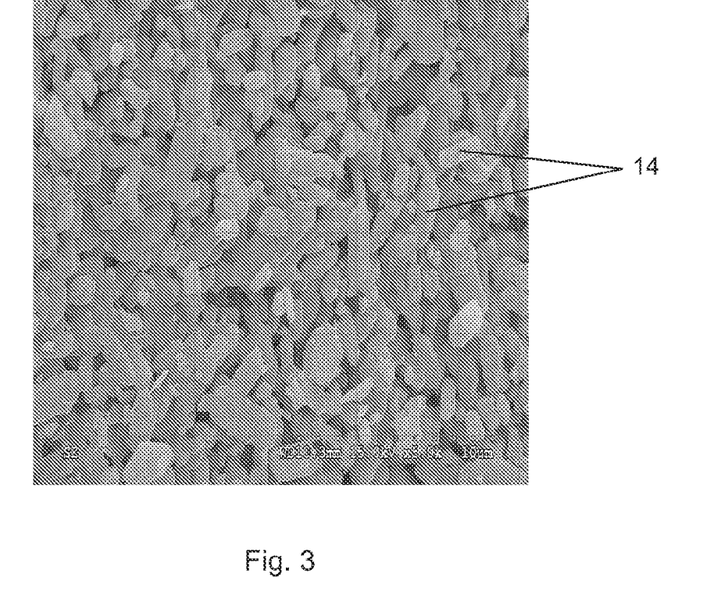
FIG. 3 is a SEM image of the calcium sulfate composite particle of FIG. 2, at 5000× magnification, showing aggregated calcium sulfate nanoparticles therein.

FIG. 1 shows a SEM image of the calcium sulfate composite particles 10 of the present invention at 100× magnification. FIG. 2 shows a SEM image of the surface 12 of a calcium sulfate composite particle 10 at 1000× magnification. FIG. 3 shows a SEM image of the calcium sulfate composite particle 10 at 5000× magnification. As shown, the composite particles 10 comprise therein aggregated crystalline nanoparticles 14 that have dimensions in nanometer range, more particularly having a diameter from about 50 to about 800 nm.

As can be appreciated, the calcium sulfate composite particles produced as described above do not contain synthetic polymers or organic solvents. Furthermore, the composite particles do not contain adhesives, as aggregation of the nanoparticles is induced by aqueous surface wetting.

It has been found that these calcium sulfate composite particles have a substantially different degradation profile from that of conventional calcium sulfate hemihydrate particles. As described in Example 1, in vitro dissolution or degradation profile of the composite particles of the present invention was determined in comparison to that of conventional medical grade calcium sulfate hemihydrate particles. The degradation profile was measured in a simulated body fluid at 37° C. The obtained degradation profile correlates to the characteristics of degradation or resorption of the material in vivo.

Figure 4:
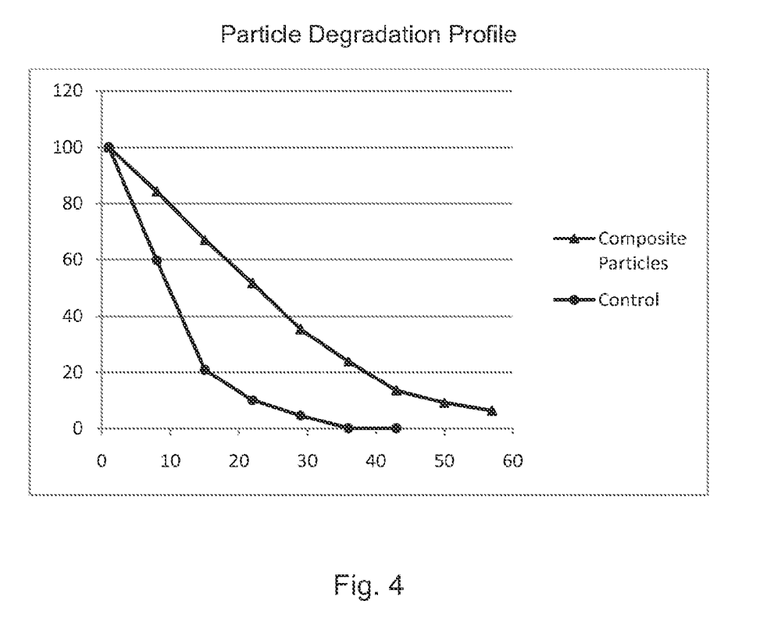
FIG. 4 shows degradation profiles of the calcium sulfate composite particles of the present invention and conventional calcium sulfate hemihydrate particles.

FIG. 4 shows the degradation profile of the two materials tested. As shown, consistent with that known in the art conventional calcium sulfate hemihydrate particles degraded rapidly, and lost 80% of their index weight by about 15 days. Substantially different from the conventional calcium sulfate hemihydrate particles, the degradation rate of the composite particles of the present invention was substantially lower and the composite particles lost the same percentage weight at about 38 days. As shown, the composite particles degraded in a substantially linear manner in a period of about 43 days, and at this time there were about 15% of the composite particles remaining. Thereafter, the rate of degradation further decreased, and at 57 days there were about 7% of composite particles remaining. This second phase of slower degradation is attributed to the conversion of calcium sulfate to calcium phosphate in the simulated body fluid used in the test. The latter has a much slower degradation rate in vitro and in vivo.

The above illustrated substantially slower and linear degradation of the composite particles of the present invention matches with the rate of new bone growth in vivo and is particularly desirable and advantageous in stimulating bone growth and repairing bone defects.

The degradation of the calcium sulfate composite particles of the present invention can be characterized using the mean half-life of the particles under the simulated dissolution condition in vitro, which represents or closely correlates with degradation of the particles in vivo. The mean half-life of the particles is defined as the time point at which 50% of the initial weight of the particles is lost. The mean half-life of the calcium sulfate composite particles of the present invention is no less than 18 days, preferably from about 20 to about 45 days. It is noted the mean half-life is a distinct property of the composite particles, determined by the structure and composition of the particles, and is substantially independent of the particle size within the size range from 200 to 1,200 μm.

As shown in FIG. 4, the mean half-life of conventional calcium sulfate hemihydrate particles under the same test condition is about 10 days. Therefore, the mean half-life of the calcium sulfate composite particles of the present invention is twice or more of the mean half-life of conventional calcium sulfate hemihydrate particles. This desirable property overcomes the deficiency of conventional calcium sulfate particles in repairing bone defects, where the conventional calcium sulfate particles dissolve substantially faster than the speed of bone growth.

When in use, the calcium sulfate composite particles are mixed with a setting agent to form a paste. Suitable setting agents are described in further detail below. In one application, the paste is directly filled into a recipient site, and then set into a solid filling. The solid filling degrades in the recipient site. In another application, the paste can be coated on the surface of an implant, and then the coated implant is introduced into the recipient site, prior to setting or after setting of the paste on the implant. In a further application, the paste can be set first into a desired shape or configuration, for example in a mold, to form an implant. Then, the preformed implant is placed in a recipient site. As the calcium sulfate composite particles degrade slowly in vivo, they leave behind a calcium phosphate lattice that further stimulates bone regeneration in the bone defects grafted with the calcium sulfate composite particles. Because of the long mean half-life, in other word a controlled degradation profile, of the composite particles, they provide bone regeneration stimulus over a prolonged period, and hence result in bone regeneration.

As described above, the calcium sulfate composite particles can be used alone as an implant material for bone argumentation. Alternatively, the calcium sulfate composite particles can also be used in conjunction with other calcium sulfate particles for bone argumentation as described hereinafter.

In a further embodiment, the present invention provides a bone grafting material that comprises a mixture of the calcium sulfate composite particles of the present invention having a diameter in a range from about 200 to about 1,200 μm, and a second type of calcium sulfate particles having a diameter from about 2 to about 60 μm. The ratio of the calcium sulfate composite particles to the second type of calcium sulfate particles in the bone grafting material is from 1:1 to 4:1, preferably from 1.5:1 to 3:1. In one embodiment, the second type of calcium sulfate particles is conventional calcium sulfate particles. The conventional calcium sulfate particles can be calcium sulfate hemihydrate, calcium sulfate dihydrate, or mixture thereof. Preferably, conventional calcium sulfate hemihydrate particles are used, and more preferably, conventional medical grade calcium sulfate hemihydrate particles are used.

When in use, the bone grafting material comprising the mixture of the composite particles and conventional calcium sulfate particles is mixed with a setting agent to form a paste. The paste can be applied in the same manner described above. The paste is set into a heterogeneous solid complex, wherein the larger composite particles are dispersed in a matrix formed by the conventional calcium sulfate hemihydrate particles.

Suitable setting agents include water, alkaline metal salt solutions such as a saline solution, or an accelerant aqueous solution containing potassium salt. The speed of setting can be controlled from a few minutes to one hour, depending on the setting agent used as well as desired surgical application. Among various setting agents, potassium salt solutions result in the fastest setting. For the purpose of the present invention, an aqueous solution containing potassium or sodium ions are preferably used. More preferably, an aqueous solution containing potassium ions can be used. Suitable examples of potassium salts include potassium sulfate, potassium phosphate, and potassium fluoride. The concentration of potassium ion controls the speed of setting, the higher it is the faster the setting process. The concentration of the potassium salt is in a range from 1% to 10%, preferably from 2% to 6%.

As can be appreciated, the composite particles and conventional calcium sulfate particles have substantially different mean half-life, as such the matrix formed by the conventional calcium sulfate particles dissolves rapidly leaving behind the composite particles. At the initial stage, the composite particles dispersed in the matrix may dissolve even slower than in the paste formed by the composite particles alone, because of the presence of surrounding matrix and relatively high local concentration of calcium sulfate from the dissolution of the matrix. As the matrix dissolves, the composite particles dissolve with a substantially slower rate in a linear manner as described above. Consequently, a relatively high concentration of calcium sulfate is present for an extended period of time due to combined effect from dissolution of the matrix and the composite particles. Therefore, the unique bone grafting material also provides a controlled degradation profile, and is particularly beneficial for providing bone regeneration stimulus over an extended period of time.

Moreover, the bone grafting material comprising the mixture of the composite particles and conventional calcium sulfate particles is easier to form a paste than using the composite particles alone, and hence easier for handling by the user.

The calcium sulfate composite particles or the bone grafting material of the present invention described above can be provided as a kit, which may further include a packaged setting agent. Instruction on how to use the calcium sulfate composite particles or the bone grafting material in accordance with the present invention is included with the kit.

The calcium sulfate composite particles or the bone grafting material of the present invention can be used clinically for bone augmentation and repairing bone defects, which includes treating any damaged area of bone. Suitable applications include dental and orthodontic applications, such as maxillofacial reconstruction, repairing bone defects around dental implants, bone augmentation of alveolar ridge, alveolar socket preservation; orthopedic and medical applications, such as repairing bone fractures or other disruption of the integrity of bone tissue, surgical reattachment of bone fragments, reconstructive surgery to assist new bone formation at sites where necessary, joint fusions, replacement of necrotic bone segments, repairing tumor cavities after tumor removal, and other suitable applications in dental and medical implantation procedures. These clinical applications include procedures for human and/or veterinary subjects, which include all non-human vertebrates.

Example 2 illustrates an example of using the bone grafting material of the present invention in repairing bone defects in vivo in an animal study. The bone grafting material was a mixture of the composite particles and medical grade conventional calcium sulfate hemihydrate particles in a ratio of 65:35. The composite particles had a diameter from about 400 to about 1,000 μm. The bone grafting material was mixed with a setting agent and set in molds to form pre-molded implants. The implant had a disk shape of 11 mm in diameter and 3 mm in thickness.

New Zealand white rabbits were used in this study. Circular defects of 11 mm in diameter were created in the parietal bones of the skull on either side of the sagittal suture line. One implant disk was surgically implanted into each of the circular defects created. The calvarial bone at the implant area was harvested after sacrifice of the test animals at 4, 8 and 16 weeks after placement of the implants. Micro computed tomography analysis (Micro CT) and histopathological analysis of the specimens were used to evaluate the response at the implant area and the effect of the bone grafting material of the present invention.

Figure 5:
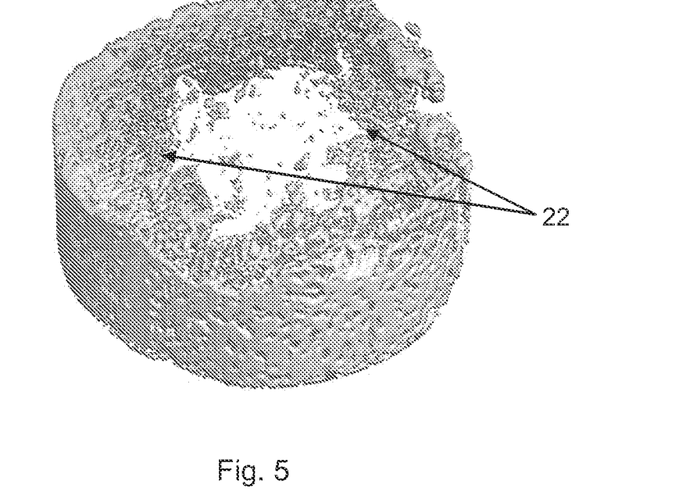
FIG. 5 is a Micro CT image of a specimen from a rabbit sacrificed at four weeks after bone grafting as described in Example 2.

As shown in FIG. 5, Micro CT analysis of a specimen harvested at four weeks after placement of the implant showed radiopaque ceramic deposits resembling bone formation from outside in at the periphery of the grafted area. Histology images confirmed that these deposits were mainly newly formed bone 22, deposited on the periphery of the defect, see FIGS. 5A-5B. The histology image further showed active osteoblasts 24 indicating strong osteoblastic activity at the periphery of the defect where new immature bone started to grow, see FIG. 5C.

Figure 6:
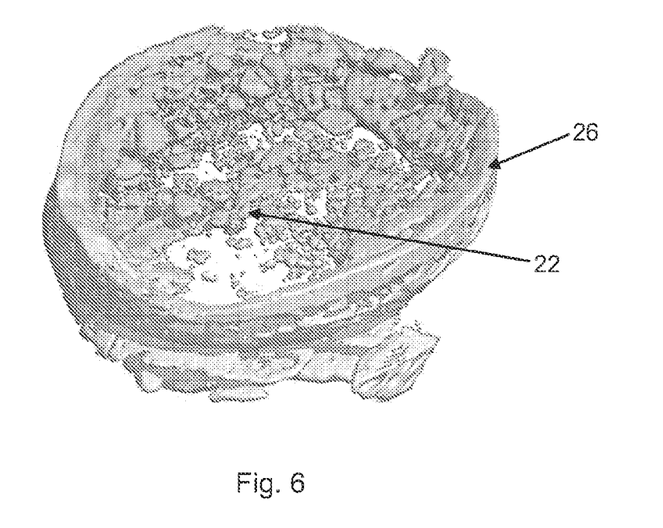
FIG. 6 is a Micro CT image of a specimen from a rabbit sacrificed at eight weeks after bone grafting.
Figure 6A:
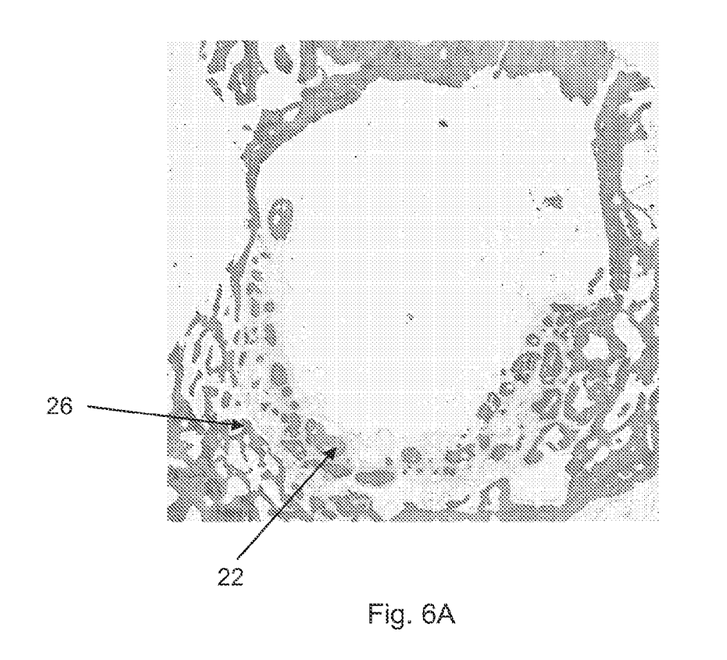
FIG. 6A is a histology image showing the entire cross-section of the explanted area at eight weeks.
Figure 6B:
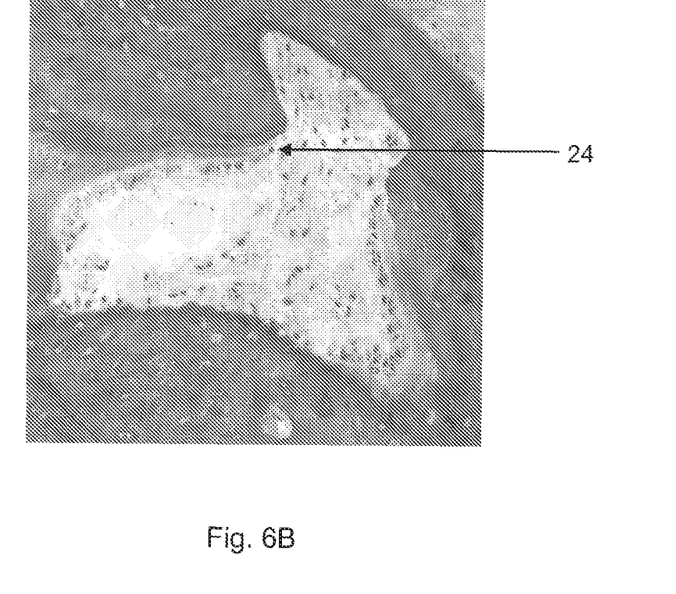
FIG. 6B is a high magnification view of the histology image of FIG. 6A.

FIGS. 6-6B illustrates Micro CT and histology images of specimens from the test animals sacrificed at eight weeks after placement of the implants. As shown by Micro CT image, almost 17% area covered with newly deposited bone at eight weeks. Mature bone 26 was observed at the periphery of the defect and growth of new immature bone 22 continued towards the center. Histologically, excellent bone response was observed. As shown in FIG. 6A, new bone 26 deposited at the periphery of the defect matured and immature bone 22 continued to grow towards the center of the defect. As further shown in FIG. 6B, active osteoblasts 24 were seen growing in the original defect area. Histomorphometrical analysis showed about 22% of the defect area covered with bone.

Figure 7:
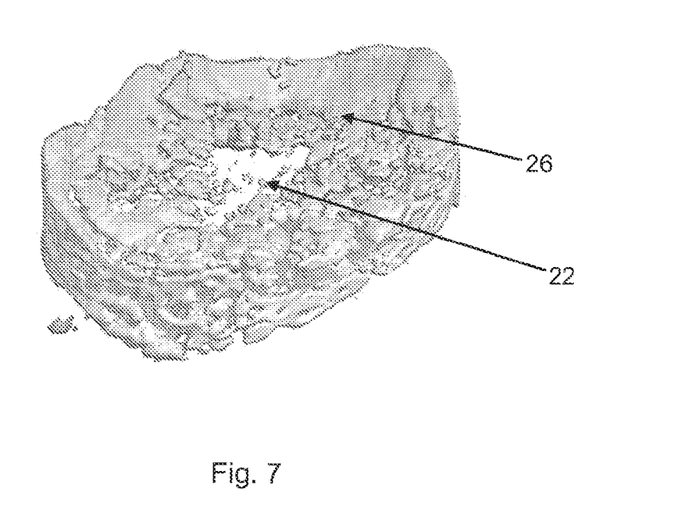
FIG. 7 is a Micro CT image of a specimen from a rabbit sacrificed at sixteen weeks after bone grafting.
Figure 7A:
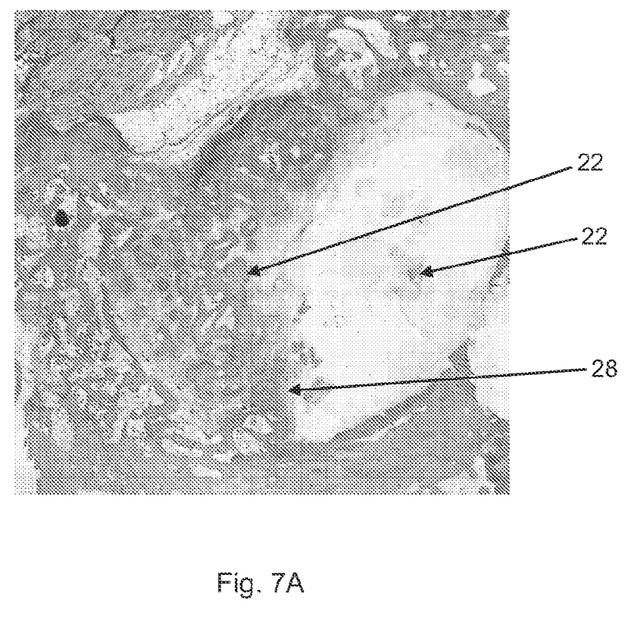
FIG. 7A is a histology image showing the entire cross-section of the explanted area at sixteen weeks.
Figure 7B:
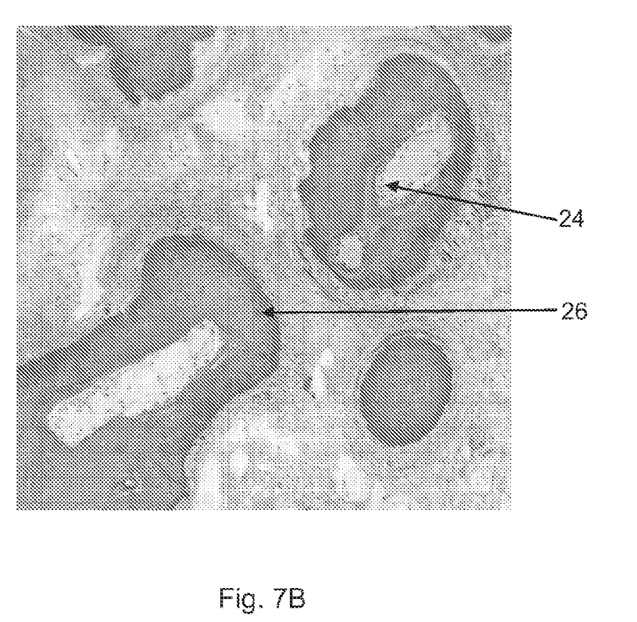
FIG. 7B is a high magnification view of the histology image of FIG. 7A.

As shown in FIG. 7, at 16 weeks after placement of the implants, new bone continued to mature from periphery of the defect towards the center as indicated at 26 and new immature bone 22 was seen at the center of the defect at this time. Histological analysis showed that bone 26 formed towards the periphery of the defect was now matured, new immature bone 22 observed on the inside of the mature bone, and deposition of bone was observed all the way to the center of the defect area, see FIGS. 7A-7B. Moreover, calcium phosphate deposits 28 were observed towards the center of the defect. As further shown in FIG. 7B, strong activity of osteoblasts 24 was observed at this time. Furthermore, histomorphometrical analysis showed that at 16 weeks 27.8% of the defect area was filled with bone.

In the animal study described in Example 2, 11 mm defects were created in rabbit calvaria. This size of defects has been referred to as critical sized defects. This means the defects do not heal by themselves. Therefore, this is a very difficult model in assessing the bone regeneration potential of a graft material. In spite of the difficult model presented, almost 28% bone growth was observed in these defects at 16 weeks, when the defects were grafted with the bone grafting material of the present invention. Moreover, the extent of 28% bone growth achieved in this study is higher than the known extent of bone growth using calcium sulfate alone as the bone grafting material.

These remarkable results demonstrate that the composite particles and the bone grafting material of the present invention are particularly advantageous in bone argumentation and repairing, which can be attributed to their ability to provide bone regeneration stimulus over a prolonged period because of the controlled degradation profile.

On the other hand, different from the known polymer containing calcium sulfate particles that share the slow degradation property, the composite particles of the present invention are free from any organic solvent used in preparing the polymer containing calcium sulfate particles, and free from any synthetic polymers. This eliminates potential side effects associated with polymers and residual solvents, reduces material and production costs, and reduces manufacturing complexity.

In a further embodiment, the composite particles, the bone grafting material, or the composition of the present invention may be used as a vehicle to deliver growth factors, antibiotics, or other medicines to the recipient site. The substance, namely growth factors, antibiotics, or other medicines, may be incorporated into the composite particles, such as by spraying during the production process or coating on the surface of the particles. Alternatively, the substance may be mixed into and provided together with the powder of the bone grafting material described above. In a further manner, the substance may be mixed with the composite particles or the bone grafting material at the time the paste is prepared using the setting agent, as such the formed composition contains the substance.

Suitable antibiotics include aminoglycosides, such as gentamycin and tobramycin, penicillins, such as amoxicillin, fluoroquinolones, such as ciprofloxacin and moxifloxacin, cephalosporins such as ceftriaxone, and others suitable for treating infections in the recipient site. The solid composition formed after setting comprises both calcium sulfate and antibiotics, and such a combination provides effective treatments of bone defect and infection simultaneously.

Suitable growth factors include, but not limited to, bone morphogenetic protein 2 (BMP2), platelet-derived growth factor (PDGF), transforming growth factor (TGF), fibroblast growth factor (FGF), vascular endothelial growth factor (VEGF), brain derived neurotrophic factor (BDNF), and insulin-like growth factor (IGF-I), epidermal growth factor (EGF), and combinations thereof. The release of growth factor into the recipient site as the solid composition degrades stimulates bone growth.

The use of a bone graft material as a delivery vehicle for growth factor is preferable to stimulate rapid bone formation in a defect. While the bone graft material alone may stimulate enough bone formation in small defects in young patients, there are patients, such as elderly, immuno-compromised, diabetic etc., and large bone defects where a stronger stimulus may be required to avoid nonunion or delayed healing. It is known that there are over six million cases of fracture in the United States alone every year, and almost 10% of fractures result in delayed healing or non union. Thus, the combination of the bone graft material of the present invention and a growth factor provides improved treatment in these cases.

It has been shown previously by Rosenblum et al ("Diffusion of fibroblast growth factor from a plaster of Paris carrier" *J. Appl. Biomater.* 1993; 4(1):67-72)), fibroblast growth factor was released in an active form from a plaster of Paris carrier and the rate of release of the growth factor was directly proportional to the degradation rate of calcium sulfate.

As shown above, the composite particles of the present invention have a long mean half-life. The slow and substantially linear degradation of the composite particles is particularly advantageous in delivery of growth factors, since it is desirable that a delivery vehicle releases growth factor in the defect site continuously and/or consistently during early as well as late periods after implantation in vivo. This continuous and consistent delivery overcomes the deficiency of most commonly used delivery vehicles, where the "burst release" model is followed. Under such a model, the growth factor is released during the first few days (or hours) after implantation of the vehicle in vivo and very little is released thereafter. Therefore, during the initial period after implantation, intrinsic growth factors are present in the defect site in abundant quantities. However, at later periods, the quantity of growth factor present diminishes.

Moreover, a combination of a calcium-phosphate based material and platelet derived growth factor (PDGF), and collagen in combination with rhBMP-2 have been used for bone grafting. However, neither collagen nor calcium-phosphate undergoes linear degradation. As such, collagen and calcium-phosphate bone graft material release most of included growth factor following the burst profile. In contrast, as demonstrated above the composite particles of the present invention degrade substantially linearly in a prolonged period. Therefore, the present invention provides a superior delivery mechanism to the collagen or calcium-phosphate based bone-graft material.

The following examples are illustrative of the invention and are in no way to be interpreted as limiting the scope of the invention, as defined in the claims.

Example 1

Degradation profile of the calcium sulfate composite particles of the present invention described above was determined in vitro in comparison to conventional calcium sulfate hemihydrate particles. The composite particles had a diameter in range from about 400 to about 1,000 μm. The medical grade conventional calcium sulfate hemihydrate particles tested had a diameter in a range from about 2 to about 60 μm.

The composite particles were weighed, wrapped in porous nylon mesh, weighed again. Mesh-wrapped composite particles were incubated for one hour in simulated body fluid (SBF) prepared according to the standard protocol (Kim et al, Process and Kinetics of Bonelike Apatite Formation on Sintered Hydroxyapatite in a Simulated Body Fluid, *Biomaterials* 2005, 26:4366-4373). After incubation, the mesh-wrapped composite particles were removed from the SBF, blot-dried, and weighed again, and this last weight was designated the index weight. The mesh-wrapped composite particles were then placed in a 25 ml plastic tube containing 5 ml of SBF, and tubes were suspended in a 37° C. water bath. The conventional calcium sulfate hemihydrate particles were subjected to the same treatment.

On day 8, 15, 22, 29, 36, 43, 50 and 57, following immersion in SBF both types of particles were removed from the SBF, blot-dried, their weight recorded, and reimmersed in fresh SBF. This was performed to an end point of 60 days or when the particles had completely dissolved.

Microsoft Excel was used to create dissolution or degradation profile for the composite particles and the conventional calcium sulfate hemihydrate particles. FIG. 4 showed the test results, the data points in the curves were an average of three samples. As shown, the degradation rate of the composition particles of the present invention was substantially lower than that of conventional calcium sulfate hemihydrate particles (the latter was indicated as control in FIG. 4). The conventional calcium sulfate hemihydrate particles lost a mean 80% of their index weight by about 15 days. The composite particles lost the same percentage weight at about 38 days. The mean half-life of the conventional calcium sulfate hemihydrate particles was about 10 days, and that of the composite particles was about 23 days.

Example 2

In vivo response to the bone grafting material of the present invention was evaluated in an animal study.

New Zealand white rabbits were used in this study. The rabbits were shaved and aseptically prepared for surgery. The surgical site was draped and an incision was made along the sagittal suture of the skull through both skin and periosteum, which was retracted to reveal the calvarial bone beneath. Circular defects of 11 mm in diameter were created with a hand drill and trephine bit in the parietal bones of the skull on either side of the sagittal suture line. Care was taken not to violate the sagittal suture or to interrupt the dura beneath the bone. The drilled bone was removed and the circular defects were filled using the bone grafting material of the present invention.

The bone grafting material of the present invention was a mixture of the composite particles and medical grade conventional calcium sulfate hemihydrate particles in a ratio of 65:35 (weight by weight). The composite particles had a diameter from about 400 to about 1,000 μm and the medical grade conventional calcium sulfate hemihydrate particles had a diameter from about 2 to 60 μm. The bone grafting material was mixed with saline as a setting agent and set in molds to form pre-molded implants. The implant had a disk shape of 11 mm in diameter and 3 mm in thickness. Each implant disk also had a small flange (about 1×15 mm) on the outer side to help keeping the implant in place. One implant disk was placed into each of the circular defects created. The periosteum and skin were sutured in layers, and the rabbits were allowed to recover in the AAALAC-approved facility where they received water and food ad libitum.

After operating on the rabbits and before sacrificing them, following examinations were done daily: gross examination of the surgical site for gross signs of local function; monitoring water intake and urine output for signs of renal function; monitoring appetite and fecal output for signs of gastrointestinal function; and monitoring demeanor and behavior for signs of nervous function. The rabbits were sacrificed in three groups at 4, 8 and 16 weeks after the implant placement.

Analysis of Specimens: After sacrifice, gross examination of the implant area was performed. The calvarial bone at the implant area was harvested after sacrifice. The specimens were preserved in 70% ethanol and dehydrated in increasing concentrations (70:30, 80:20, 90:10, and 100%) of ethyl alcohol. Ethanol adequately preserved the tissue, stopped dissolution of calcium sulfate components, and preserved mineral structure. The samples were finally infiltrated and embedded in hard poly methyl methacrylate (PMMA).

Micro Computed Tomography analysis (Micro CT): Embedded and unembedded samples were examined using a Scanco 40 MicroCT system (Scanco Medical, Bassersdorf, Switzerland). Planar images and three-dimensional reconstructions were used to examine local bone response and degradation of the bone grafting materials, and to measure volumetric amounts of bone and bone grafting material present.

Sectioning of Embedded Specimens: A Buehler Isomet™ low speed saw and Petro-Thin diamond wafering blade/grinding system was used to obtain histological sections of 80-120 μm thick. These sections were polished to a 1200 grit finish and examined using both scanning electron microscope (in back scattered electron imaging and x-ray microanalysis modes) and light histopathology.

Histopathological Analysis: The cut sections were stained with Stevenel's Blue differential tissue staining protocol (SVG). SVG stains soft tissue green-blue, muscle blue-green, cartilage violet-blue and mineralized tissue red to orange. The stained sections were also examined microscopically with an APERIO Scanscope System.

Statistical Analysis: The amount of new bone formed in each of the defects was calculated through histomorphometric analysis using Qwin Software.

Results:

Routine Observations: All animals healed well. All rabbits were bright, alert and responsive during the course of stay before sacrifice. All rabbits expressed normal, curious behavior indicating normal brain function, and had regular and normal water intake and urine output indicating normal renal function. The rabbits had regular and normal appetite, fecal output and bowel movement indicating regular gastrointestinal function. No signs of systemic disease were observed, and no significant signs of pain were observed.

Figure 5A:
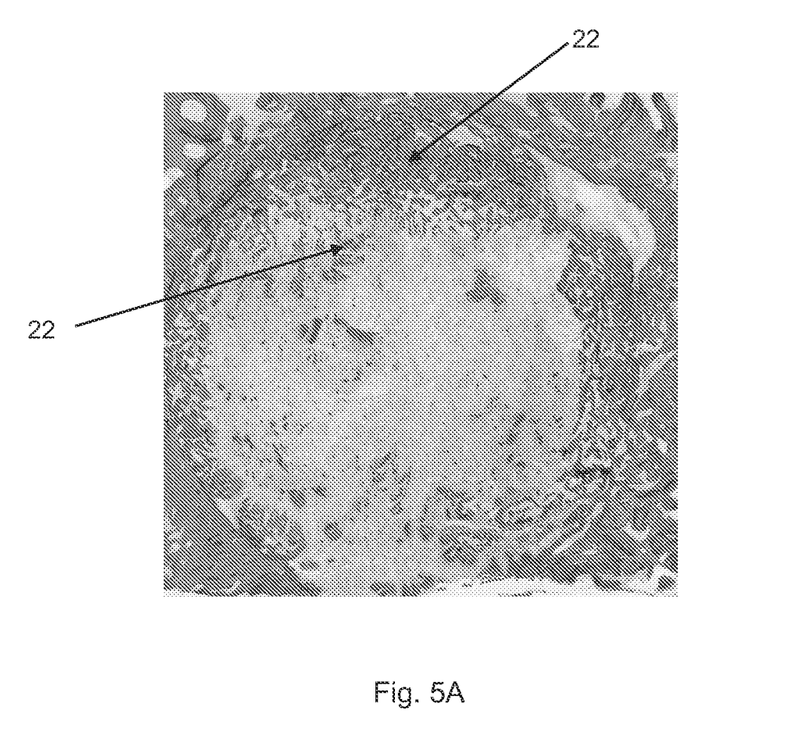
FIG. 5A is a histology image showing the entire cross-section of the explanted area at four weeks.
Figure 5B:
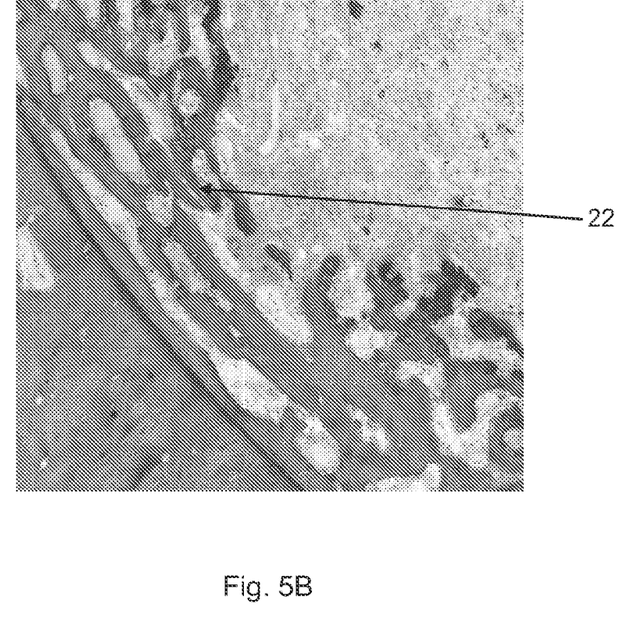
FIG. 5B is a high magnification view of the histology image of FIG. 5A.
Figure 5C:
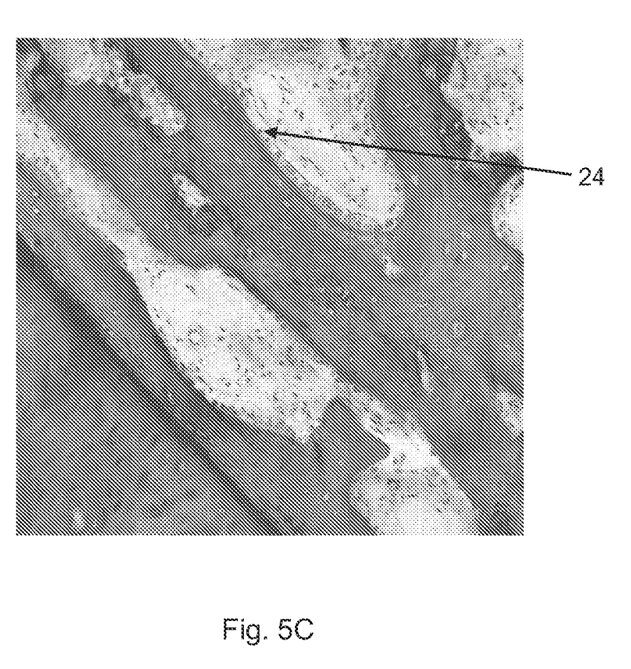
FIG. 5C is a further high magnification view of the histology image of FIG. 5A.

4 Week Observations: All surgical sites and animals healed well. On gross examination, no adverse reaction was noted. FIG. 5 is a Micro CT image of a specimen from a rabbit sacrificed at four weeks, showing radiopaque ceramic deposits resembling bone formation from outside in at the periphery of the grafted area, as indicated at 22. Histology images confirmed that these deposits were mainly newly formed bone, deposited on the periphery of the defect, see FIGS. 5A-5C. FIG. 5A is a histology image showing the entire cross-section of the explanted area at four weeks. As shown, immature bone 22 indicating new bone growth was observed at the periphery of the defect. It grew towards the center of the defect. FIG. 5B shows a high magnification view of the histology image, showing new immature bone 22 at the periphery of the defect. FIG. 5C is a further high magnification view of the histology image, showing osteoblasts 24 indicating strong osteoblastic activity at the periphery of the defect where bone started to grow. The interface of the original bone and the grafted area appeared healthy.

8 Week Observations: On gross observations, all the sites were healing well. The bone grafting material degraded significantly at eight weeks. FIG. 6 shows a Micro CT image from a rabbit sacrificed at eight weeks, which showed almost 17% area covered with newly deposited bone. Mature bone 26 was observed at the periphery of the defect and growth of new immature bone 22 continued towards the center. Histologically, excellent bone response was observed. FIG. 6A shows a histology image of the entire cross-section of the explanted area. As shown, consistent with Micro CT, new bone 26 deposited at the periphery of the defect matured and immature bone 22 continued to grow towards the center of the defect. As further shown in FIG. 6B, active osteoblasts 24 were seen growing in the original defect area. Histomorphometrical analysis was performed to quantify the amount of bone present in the area, which showed about 22% of the defect area covered with bone.

16 Week Observations: All rabbits healed well. Micro CT showed ceramic deposits covering almost entire defect area. As shown in FIG. 7, new bone continued to mature from periphery of the defect towards the center as indicated at 26 and new immature bone 22 was seen at the center of the defect at this time. Histological analysis showed that new bone 26 formed towards the periphery of the defect was now matured, new immature bone 22 observed on the inside of the mature bone, and deposition of bone was observed all the way to the center of the defect area, see FIGS. 7A-7B. Moreover, calcium phosphate deposits 28 were observed towards the center of the defect, while at this time, no evidence of the bone grafting material of the implant was observed. As further shown in FIG. 7B, strong activity of osteoblasts 24 was observed.

Histomorphometrical analysis was performed to quantify the amount of bone developed in the defect area, and the results showed 27.8% of the defect area filled with bone at 16 weeks.

Each patent, patent application, publication, text and literature article or report cited or indicated herein is hereby expressly incorporated by reference in its entirety.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

What is claimed is:

1. Calcium sulfate composite particles for bone augmentation and repair, comprising aggregated calcium sulfate nanoparticles of a diameter from about 50 to about 800 nanometers (nm), said calcium sulfate nanoparticles comprising a mixture of calcium sulfate dihydrate and calcium sulfate hemihydrate; said composite particles having a diameter from about 200 to about 1,200 micrometers (μm), and having a mean half-life from about 20 to about 45 days.

2. The composite particles of claim 1, wherein said diameter of said composite particles is from about 400 to about 1,000 μm.

3. The composite particles of claim 1, wherein said composite particles degrade in a linear manner.

4. The composite particles of claim 1, wherein said composite particles are produced by aqueous spraying and rotationally mixing conventional calcium sulfate hemihydrate particles at elevated temperature, thereby forming said aggregated calcium sulfate nanoparticles comprising the mixture of calcium sulfate dihydrate and calcium sulfate hemihydrate.

5. The composite particles of claim 1, wherein said composite particles further comprise one or more growth factor or antibiotics.

6. A bone grafting material for bone augmentation and repair, comprising:
  (a) calcium sulfate composite particles having a diameter from about 200 to about 1,200 μm, said composite particles comprising aggregated calcium sulfate nanoparticles having a diameter from about 50 to about 800 nm, said calcium sulfate nanoparticles comprising a mixture of calcium sulfate dihydrate and calcium sulfate hemihydrate; said composite particle having a mean half-life from about 20 to about 45 days; and
  (b) a second type of calcium sulfate particles having a particle diameter from about 2 to about 60 μm,
  wherein a ratio of said calcium sulfate composite particles to said second type of calcium sulfate particles in said composition is from 1:1 to 4:1.

7. The bone grafting material of claim 6, wherein said diameter of said calcium sulfate composite particles is from about 400 to about 1,000 μm.

8. The bone grafting material of claim 6, wherein the ratio of said calcium sulfate composite particles to said second type of calcium sulfate particles in said composition is from 1.5:1 to 3:1.

9. The bone grafting material of claim 6, wherein said second type of calcium sulfate particles comprises calcium sulfate hemihydrate, calcium sulfate dihydrate, or mixture thereof.

10. The bone grafting material of claim 6, wherein said bone grafting material further comprises one or more growth factor or antibiotics.

11. A method for bone augmentation comprising:
  (a) mixing a bone grafting material with a setting agent to form a composition; said bone grafting material comprising calcium sulfate composite particles having a diameter from about 200 to about 1,200 μm, said composite particles comprising aggregated calcium sulfate nanoparticles of a diameter from about 50 to about 800 nm, said calcium sulfate nanoparticles comprising a mixture of calcium sulfate dihydrate and calcium sulfate hemihydrate; said composite particle having a mean half-life from about 20 to about 45 days; and
  (b) applying said composition to a recipient site;
  wherein said calcium sulfate composite particles degrade at a rate determined by said mean half-life, and affect a prolonged stimulation to bone growth in said recipient site.

12. The method of claim 11, wherein said bone grafting material further comprises a second type of calcium sulfate particles having a particle diameter from about 2 to about 60 μm, wherein a ratio of said calcium sulfate composite particles to said second type of calcium sulfate particles in said bone grafting material is from 1:1 to 4:1; and wherein said composition comprises said calcium sulfate composite particles dispersed in a matrix formed by said second type of calcium sulfate particles.

13. The method of claim 12, wherein said second type of calcium sulfate particles degrade faster than said calcium sulfate composite particles in said recipient site.

14. The method of claim 11, wherein applying said composition is filling said recipient site with said composition as a paste before setting.

15. The method of claim 11, wherein applying said composition is placing said composition into said recipient site after setting.

16. The method of claim 11, wherein said calcium sulfate composite particles degrade in a linear manner.

* * * * *